United States Patent [19]
Maytal

[11] Patent Number: 5,603,221
[45] Date of Patent: Feb. 18, 1997

[54] MULTIPROBE SURGICAL CRYOGENIC APPARATUS

[75] Inventor: Ben-Zion Maytal, Atlit, Israel

[73] Assignee: State of Israel, Ministry of Defense, Rafael-Armaments Development Authority, Haifa, Israel

[21] Appl. No.: 496,685

[22] Filed: Jun. 29, 1995

[30] Foreign Application Priority Data

Jun. 30, 1994 [IL] Israel ......................................... 110176

[51] Int. Cl.$^6$ .............................. F25B 19/02; A61B 17/36
[52] U.S. Cl. ................................. 62/51.2; 62/657; 62/293; 606/24
[58] Field of Search .................... 62/51.2, 259.3, 62/293, 657; 128/DIG. 27; 606/23, 24, 25

[56] References Cited

U.S. PATENT DOCUMENTS

| | | | |
|---|---|---|---|
| 3,439,680 | 4/1969 | Thomas, Jr. | 606/24 |
| 3,948,269 | 4/1976 | Zimmer | 606/24 |
| 4,146,030 | 3/1979 | Holroyd | 62/293 X |

FOREIGN PATENT DOCUMENTS

| | | | |
|---|---|---|---|
| 649741 | 4/1992 | Australia | 606/24 |
| 0064741 | 4/1992 | Australia | 606/24 |
| 0608927A2 | 8/1994 | European Pat. Off. . | |
| 0651308A1 | 5/1995 | European Pat. Off. . | |
| 774549 | 10/1980 | U.S.S.R. . | |
| 1217377 | 3/1986 | U.S.S.R. . | |
| 1422445 | 1/1976 | United Kingdom . | |

OTHER PUBLICATIONS

Andrew A. Gage, "Current Issues in Cryosurgery", Cryobiology 19, 1982, pp. 219–222.

*Primary Examiner*—William E. Wayner
*Attorney, Agent, or Firm*—Merchant, Gould, Smith, Edell, Welter & Schmidt, P.A.

[57] ABSTRACT

A cryogenic surgical apparatus comprises: a) a plurality of probes, each having a contact surface, each of which probes is suitable for creating fast temperature changes at the said contact surface; b) temperature generation means, coupled to each of the said probes, being capable of creating cryogenic and above 0° C. temperatures at the said contact surface of the said probe; and c) temperature control means, to control the said temperature generation means.

16 Claims, 5 Drawing Sheets

MULTIPROBE SURGICAL CRYOGENIC APPARATUS

FIELD OF THE INVENTION

The present invention relates to surgical apparatus. More particularly, the invention is directed to apparatus for performing cryogenic surgery.

BACKGROUND OF THE INVENTION

Cold and hot surfaces are used in the art for medical uses. For instance, cryogenic techniques are employed to destroy malignant tissues, or for plastic surgery. One example of such a use is presented in SU 774,549, which relates to a thermal treatment of biological tissues by passing heat carriers through a cryosurgical probe. The method is said to be useful in the cryo-surgery of the human brain. This method, however, involves passing a heat carrier through a surgical probe, its subsequent heating and repeated passage through the probe. Acetone or alcohol are used as the heat carrier. Prior to its passage through the probe the heat carrier is either cooled to −70°–75° C., or heated to +70°–90° C.

Device of this type present severe drawbacks, inasmuch as they have long lags in temperature changes, they require cumbersome heating/cooling apparatus outside the probe, and are complicated and expensive to use.

Cryosurgical instruments having both cryocooling and heating capabilities are also known in the art. One such device and its medical use have been described by Andrew A. Gage ["Current Issues in Cryosurgery", *Cryobiology* 19, 219–222(1982), at pp. 220–21]. The device described therein was cooled by liquid nitrogen and electrically heated, to provide hemostasis. The electrical heating, however, by its nature is a relatively slow procedure.

Another device is described in SU 1,217,377, which exploits the expansion of gases through an orifice. However, simple expansion of gas through an orifice provides relatively slow temperature changes, and the changes in temperature are relatively mild. Thus, for instance, in the device of SU 1,217,377 it is not possible to liquefy nitrogen. Additionally, this prior art device employs helium at room temperature which, expanding from a pressure of about 300 atmospheres, will attain a heating of merely about 30° C. In any case, in the single pass expansion described in this reference, liquefaction of nitrogen cannot be achieved. However, helium has an inversion temperature of about 45K, which renders it possible to employ neon or hydrogen as the second gas, as is done in this reference. The highest inversion temperature of neon is about 200K, and of hydrogen is about 180K. Accordingly, these gases cannot be used while using nitrogen as the first gas, because the temperature of liquid nitrogen is 80K, and thus the heating obtainable with neon and hydrogen is low. Additionally, neon and hydrogen may be found at an inversion temperature lower than their maximal temperature, so that no heating is obtained. However, neon is expensive and hydrogen is dangerous, and the obtainable temperatures are unsatisfactory for many uses, which accounts for the lack of success of the above-mentioned device.

Copending Israeli Patent Application No. 104506, filed Jan. 25, 1993 by the same applicant hereof, the specification of which is incorporated herein by reference, provides a method by means of which a fast and periodic change of surface temperature, even down to cryogenic range, can be created, at the desired location, in a simple and effective manner. This is achieved by creating a surface having a fast changing temperature, by providing a heat exchanger coupled to an orifice opening into a jacket which is in contact with the surface to be heated and cooled, the said jacket forming a reservoir capable of housing a fluid in contact with the surface to be heated and cooled, and providing two gas sources, each gas source being independently connected to the said heat exchanger, one source providing a first gas, which liquefies when it expands through the said orifice, and the other gas source providing a second gas, having an inversion temperature lower than the temperature obtained by the liquefaction of the first gas, and causing the exhaust gas flowing out from the said jacket, to flow through the said heat-exchanger to preheat or precool the inflowing gas, as the case may be, and further causing the said first and the said second gas alternately to flow through the said heat exchanger and orifice, to cool or to heat the said surface; means being provided for allowing and stopping the flow of each gas through the said orifice.

The selection of appropriate gases is crucial. For instance, the maximum inversion temperature of helium is 43K. thus, even when somewhat precooled by boiling nitrogen at 77.3K, it still will warm up when undergoing Joule-Thomson expansion. Furthermore, providing a preheating or precooling of the inflowing gas is not just a matter of efficiency or saving, but is an essential part of the invention, since processes and devices employing a one-pass heating or cooling, without utilizing an exchange of heat via an appropriate heat-exchanger, will not provide sufficiently low or sufficiently high temperatures, and will result in a temperature change which is excessively slow.

Heat exchangers can be of any type, and may be, e.g., a finned tube heat-exchanger or a porous-matrix heat-exchanger, e.g., of the type described in British Patent No. 1,422,445. The device described in this British patent provides only for the cryocooling of the probe, the purpose being to maintain the temperature of the probe below −80° C., thus avoiding altogether the need for heating the probe. It should be mentioned that, according to the teachings of this patent, heating was necessary, when operating at temperatures above −80° C., for the purpose of releasing the probe from the tissue which adhered to it upon touching the cold tip. However, when operating according to IL 104506, with fast cooling-heating cycles, the heat exchanger can be utilized also for heating purposes.

The first gas is preferably selected from the group consisting essentially of argon, nitrogen, air, krypton, $CF_4$, xenon and $N_2O$, and the second gas is helium.

Cryogenic liquefaction occurs at the tip of the cold extremity of the device operating according to IL 104506, under the cooled metal surface. The Linde-Hampson method is applied, using the Joule-Thomson effect for cooldown to liquefaction. IL 104506 also describes an apparatus for the cryocooling and the heating of surfaces, comprising:

1) a heat exchanger coupled to an orifice, the said orifice opening into a jacket;
2) a jacket which is in contact with the surface to be heated and cooled, the said jacket forming a reservoir capable of housing a fluid in contact with the surface to be heated and cooled;
3) two pressurized gas sources, each gas source being independently connected to the said heat exchanger;
4) means for allowing and stopping the flow of each gas through the said orifice.

The method of IL 104506 makes it possible to obtain a high frequency of temperature change. Thus, for instance, one may which, for a given application, to oscillate between temperatures of −50° C. and +100° C. only.

Copending Israeli Patent Application No. 107460, filed Nov. 1, 1993, by the same applicant hereof, the specification of which is incorporated herein by reference, provides an apparatus for creating controlled temperature changes on a contact surface, which comprises:

a) a probe having a contact surface, which probe is suitable for creating fast temperature changes at the said contact surface;

b) temperature generation means, coupled to the said probe, being capable of creating cryogenic and above 0° C. temperatures at the said contact surface of the said probe; and c) processing means to control the said temperature generation means according to predetermined operating conditions.

The temperature generation means can be of any suitable type, including but not limited to gas expansion, electric means, and their combinations. According to a preferred embodiment of IL 107460, the apparatus comprises:

a) a probe comprising:
1) heat exchanging means coupled to an orifice, the said orifice opening into a jacket;
2) a jacket which is in contact with the surface to be heated and cooled, the said jacket forming a reservoir capable of housing a fluid in contact with the surface to be heated and cooled;
3) two independent connections for pressurized gas sources, connected to the said heat exchanger;

b) two independent pressurized gas sources, connected to the said probe through the said two independent connections;

c) controllable gas flow valves to permit or preclude the flow of each of the gases from the said independent pressurized gas sources into the said probe;

d) processing means to control the said controllable gas flow rate valves according to predetermined operating conditions.

The probe used in IL 107460 can be any suitable probe, of any type and shape, which utilizes the Joule-Thomson effect. For example, the probe described in IL 104506 can be suitably used for this purpose.

The apparatus may also comprise external data input means, to provide operation data to the processing means, such as a keyboard, a communication port, e.g., RS232, or magnetic or optical reading means, to read pre-prepared data, and may further comprise display means to display data written to, or read from, the processing means. The processing means can be of any suitable type, e.g., the apparatus may be coupled to a microcomputer programmed to carry out the functions described herein, as well as any other desired auxiliary function. Additionally, imaging apparatus can be provided to follow and control the operation of the probe.

However, the devices of the known art are inadequate for carrying out complicated surgery, such as liver surgery, because it has been found that cryogenic intervention must be carried out in many cases in parallel at different locations, using temperature profiles which must be coordinated between the various locations. Furthermore, in the prior art apparatus it is necessary to change the probe, in order to use the appropriate probe size and/or shape at different locations and intervention times. This renders the use of these techniques impractical in complicated surgery, such as liver, lung or brain surgery, as time is of the essence, and changing the probe is a time-consuming operation. Additionally, prior art devices are controlled from remote control panels, and this hampers the operation of the surgeon who has to be assisted by another person in operating the heating/cooling cycles, or needs to shift his attention from the patient to the controls.

SUMMARY OF THE INVENTION

It is an object of the present invention to provide an apparatus which overcomes the shortcomings of known apparatus.

It is another object of the invention to provide apparatus which can be used to perform simultaneous multi-site cryogenic surgery.

It is a further object of the invention to provide an apparatus which makes it possible to carry out cryogenic surgery employing complex temperature strategies.

It is still another object of the invention to provide apparatus which is effective, simple and convenient to operate.

It is still a further object of the invention to provide surgical apparatus which can be fully controlled by the surgeon, without the need to revert to distant control panels.

Other objectives of the invention will become apparent as the description proceeds.

The invention is primarily directed to cryogenic surgical apparatus, comprising:

a) a plurality of probes, each having a contact surface, each of which probes is suitable for creating fast temperature changes at the said contact surface;

b) temperature generation means, coupled to each of the said probes, being capable of creating cryogenic and above 0° C. temperatures at the said contact surface of the said probe; and c) temperature control means, to control the said temperature generation means.

According to a preferred embodiment of the invention, the apparatus comprises:

a) a plurality of probes, each probe comprising:
1) heat exchanging means coupled to an orifice, the said orifice opening into conduit means, e.g., a jacket;
2) conduit means in contact with the surface to be heated and cooled, the said conduit means being suitable to allow the flow of a fluid in contact with the surface to be heated and cooled;
3) two independent connections for pressurized gas sources, connected to the said heat exchanger;

b) two independent pressurized gas sources, connected to the said probe through the said two independent connections;

c) controllable gas flow valves to permit or preclude the flow of each of the gases from the said independent pressurized gas sources into the said probe;

d) control means, to control the said controllable gas flow rate valves according to desired probe temperatures.

According to a preferred embodiment of the invention, the temperature control means control the temperature of the contact surface of each probe, independently, in the range −170° C. to +70° C. This temperature range is the most useful for cryogenic surgery. However, the invention is not limited to such range, and different temperatures, outside the said range, can of course be used, when desired or appropriate.

According to a preferred embodiment of the invention, the apparatus further comprises temperature-reading means located at or near the contact surface, which temperature-reading means provide temperature readings to the control means. Such temperature-reading means may comprise, e.g., one or more thermocouples, but at least two thermocouples are preferred, to ensure continued feedback temperature readings. The temperature readings permit the processing means to determine whether the temperature is to be increased or decreased, in order to remain at the predetermined temperature, and to close or open the appropriate valves.

According to another preferred embodiment of the invention, the apparatus further comprises display means to display temperature and status data for each of the plurality of probes. In a preferred embodiment, the status for each probe is independently selectable from: 1) OFF; 2) STICK; 3) FREEZE and 4) THAW. OFF, represents a situation where the probe is not cooled not heated. STICK, represents a temperature of about $-10°$ to $-30°$ C. at which the contact surface of the probe is maintained, at which temperature the probe sticks to the cells being treated. This is important to maintain the probe in a desired position, while avoiding massive killing of the cells in its surroundings. FREEZE, represents a situation in which gas is being passed through the probe and the probe is cooling. THAW, represents a situation in which the probe, which was previously cooled, is being heated. The above operations can be controlled either by: 1) appropriate buttons positioned on the probe handle; or 2) by control means, e.g., the processor (for instance, a PC computer), via a control board or a keyboard; or 3) through a preset heating/cooling program entered in the control means before surgery begins.

During the operation of the apparatus of the invention, the operator can be alerted, when using pressurized gas reservoirs, of the remaining lifetime of the gas reservoir. In order to do so, in a preferred embodiment of the invention there are provided pressure-reading means located between the pressurized gas source and the probe, to provide to the processing means readings corresponding to pressure supplied by each pressurized gas source. Thus, during the emptying of a gas reservoir, its pressure decreases and the processing means, which keeps track of such pressures, can calculate the expected operation time remaining with the reservoir, on the basis of pressure changes with time in the specific operation undertaken. Furthermore, pressure-reading means can also be provided, when using a pressurized gas source other than a reservoir, to determine the working pressure in the gas line.

Of course, the pressurized gas reservoirs can be replaced by, or integrated with, any other gas source, such as a compressor or a booster.

The invention is of course not limited to any specific number of probes. However, it has been found that for practical purposes 5 probes are sufficient.

All the above and other characteristics and advantages of the invention will be better understood through the following illustrative and non-limitative description of preferred embodiment.

DETAILED DESCRIPTION OF PREFERRED EMBODIMENTS

Figure 1:
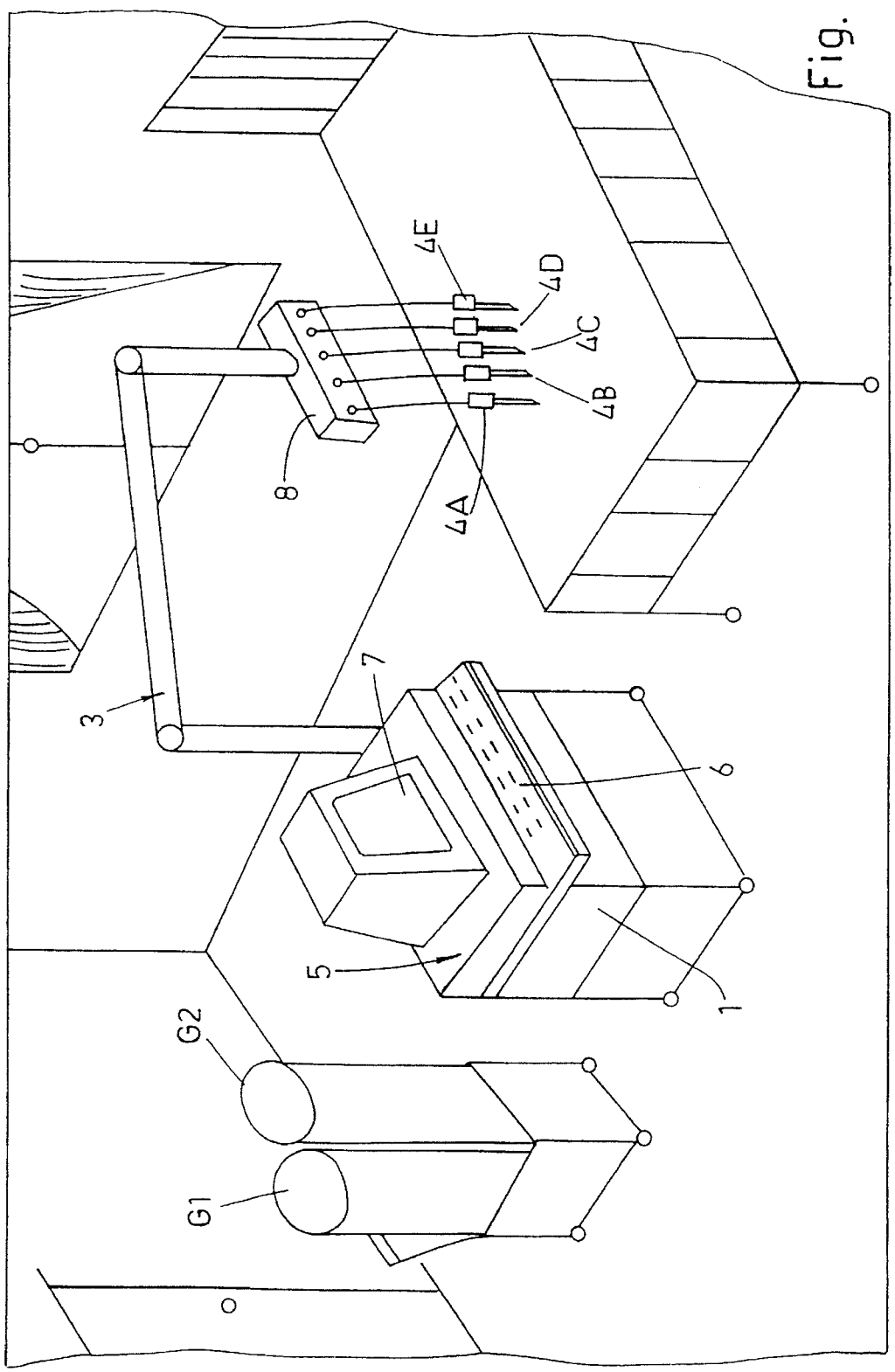
FIG. 1 is a schematic perspective view of an apparatus according to one preferred embodiment of the invention.

FIG. 1 illustrates an apparatus according to a preferred embodiment of the invention. This apparatus is designed to be movable and self-supporting, and does not require connection to outside gas sources. It consists of a body 1, provided with wheels, connected to two gas reservoirs, G1 and G2. The two gas reservoirs contain gas under pressure. An arm 3, with elbows and joints, is used to support a plurality of probes, 4A–4E.

Each probe 4A–4E is connected to the gas reservoirs and to a processor, as explained above and in further detail below. In this case, a personal computer 5 is used to control the operation of the probes. A keyboard 6 and a display 7 are provided, the purpose of which will be further described below. A control board 8 is also provided, which will be further discussed below.

Figure 2:
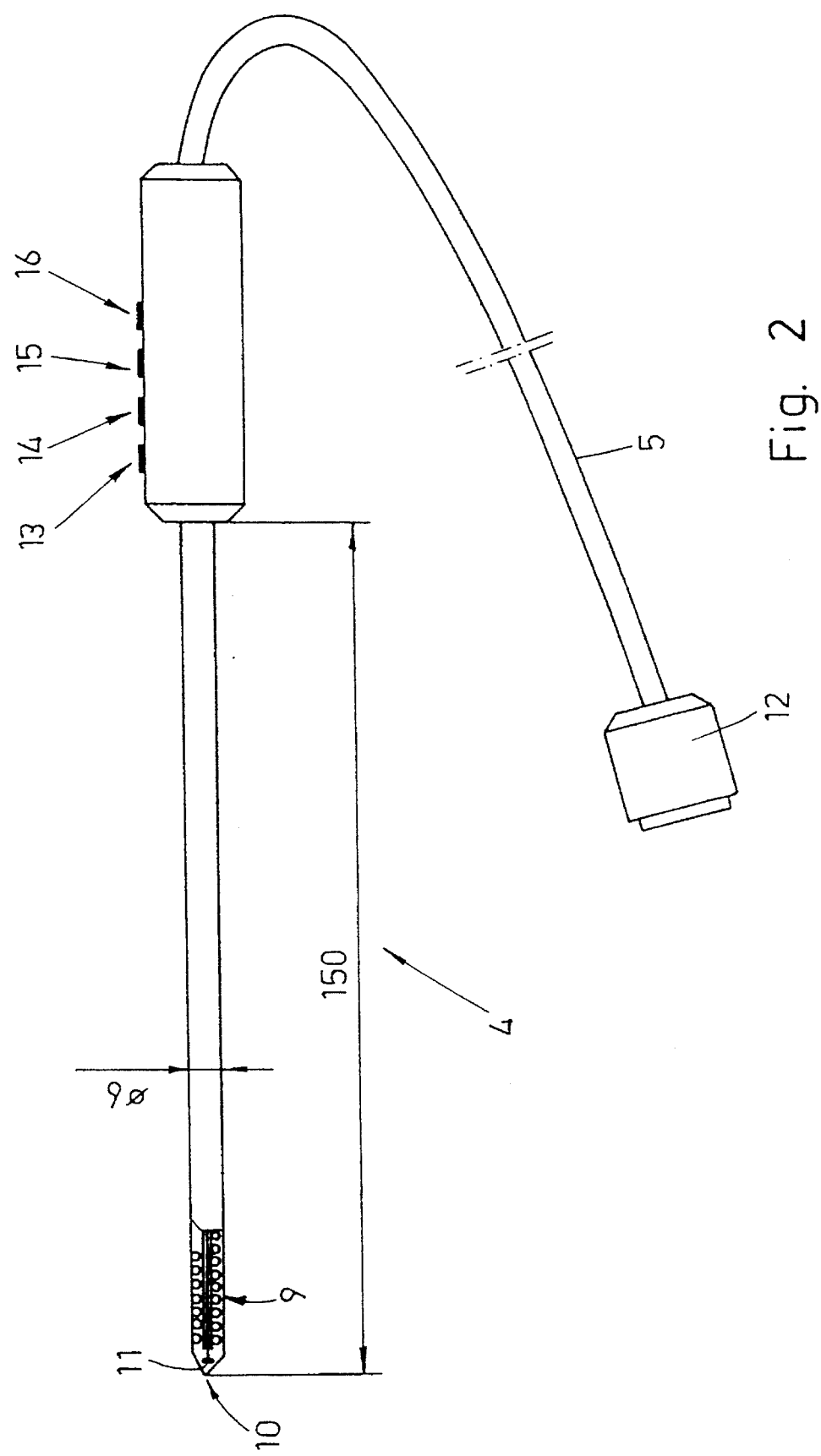
FIG. 2 schematically shows of a probe, according to one preferred embodiment of the invention, shown in partial cross-section.

FIG. 2 shows one of the probes 4A–4E of FIG. 1 in greater detail. The Joule-Thomson heat exchanger 9 serves contact surface 10, which is heated or cooled, depending on the nature of the gas flowing therethrough. Thermocouple 11 is in close contact with the inner part of contact surface 10, and detects the temperature at that location. The thermocouple wire is led to the processing means through line 5 and connector 12. Gas leaving the probe is exhausted, in this particular embodiment of the invention, to the atmosphere either through connections in the probe, or at connector 12.

The probe is provided with operating switches 13, 14, 15 and 16. These switches operate the probe towards cooling or heating, or for preset cooling/heating cycles. However, these basic control buttons can be replaced by the control means referred to above and described hereinafter, positioned either on the display, or on a separate controller, or on both, for the purpose of obtaining greater control over the process.

The switches provided on the probe are an important feature of the apparatus of the invention, because they permit full control of the probe operation by the surgeon, unlike in prior art devices where control is remote, on a control panel and by means of remote switches and valves, which limits the ability of the surgeon to control the operation of the probe. Appropriate wirings, from the switches to the control unit, are apparent to the skilled person, and are therefore not shown in the figure, for the sake of simplicity.

By way of example, typical dimensions of a probe suitable for operating on the liver are, as shown in the figure, a diameter of 6 mm and a length of 150 mm.

Specifically, the processor (in this case, the Personal Computer) is used to provide to the surgeon data on the status of the various probes, and updated data on the surgery being undertaken. These data are displayed on the display, and the surgeon may follow the instantaneous status of each probe, as well as the history of all the surgery being performed. Providing appropriate software and peripheral hardware for this purpose is, of course, within the scope of the skilled engineer, and these matters are therefore not discussed herein, for the sake of brevity.

Additionally, more data (such as medical and surgical history) can be displayed to the surgeon, either before or during surgery, for a specific patient. Relevant data can be fed to the processor via a diskette, or can be retrieved from an appropriate data bank.

The device of the invention can further be set up with different operating values, which can be stored in the processing means for use during surgery. Thus, different maximal and minimal temperatures, as well as preferred STICK temperature, can be chosen before surgery, depending on the type of tissue and the area treated. Additionally, set-ups can be provided independently for each probe, by defining the appropriate parameters before surgery. This is important in case, e.g., where an area is to be treated, part of which is near a sensitive organ which should not be inadvertently damaged by too low temperatures. In such a case, the probes intended for use near the most sensitive area can be set-up with less extreme temperatures. The actual software used to control the temperatures, cycles times and numbers, and any other operating parameter, can be easily provided by any skilled person, and is therefore not discussed herein, for the sake of brevity. The ability to control the temperatures in a fine way, however, derives from the nature of the device of the invention and from the heating/cooling method employed, prior art devices, which employ, e.g., nitrogen flow, are not easily controllable, as relatively small changes in nitrogen flow may substantially affect the temperature of the probe contact surface.

Figure 3:
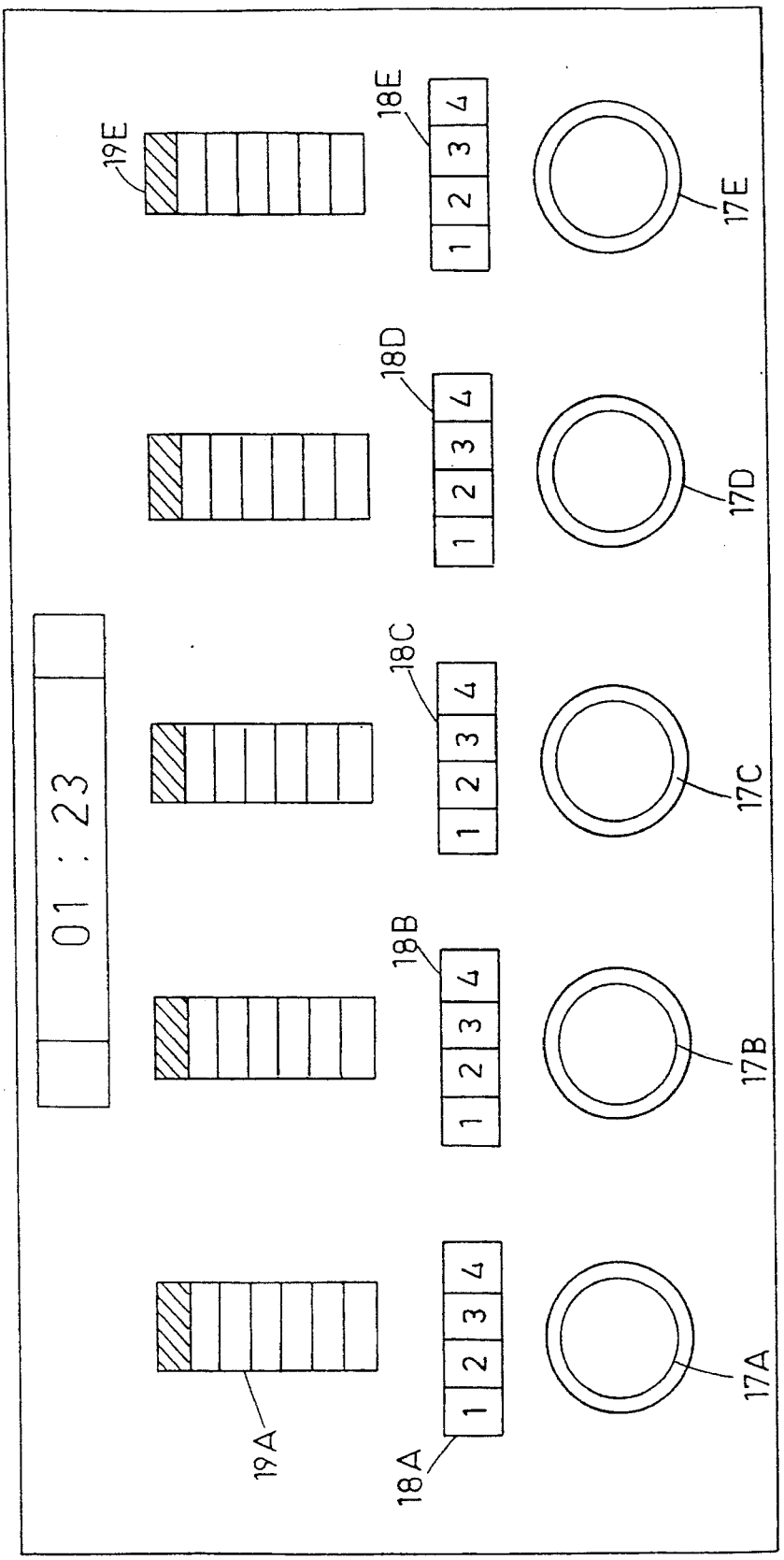
FIG. 3 schematically illustrates a probes control board.

FIG. 3 illustrates a control board 8 (FIG. 1), according to one embodiment of the invention. Each probe 4A–4E is connected to gas and data lines through connections 17A–17E in the board 8. Four sets of buttons, 18A–18E are provided, for enabling the four possible operating conditions of the probe, as discussed above. Buttons 18A–18E may be provided instead, or in addition to the buttons provided on the probe handle.

Analog temperature displays 19A–19E are also provided, to provide a quick reference for the status of each probe. A timer 20 is also provided, to time the procedure being performed. All the above information (and any other information that one may wish to provide) is positioned above the head of the surgeon, near the probes, and is therefore available for quick reference throughout surgery.

Figure 4:
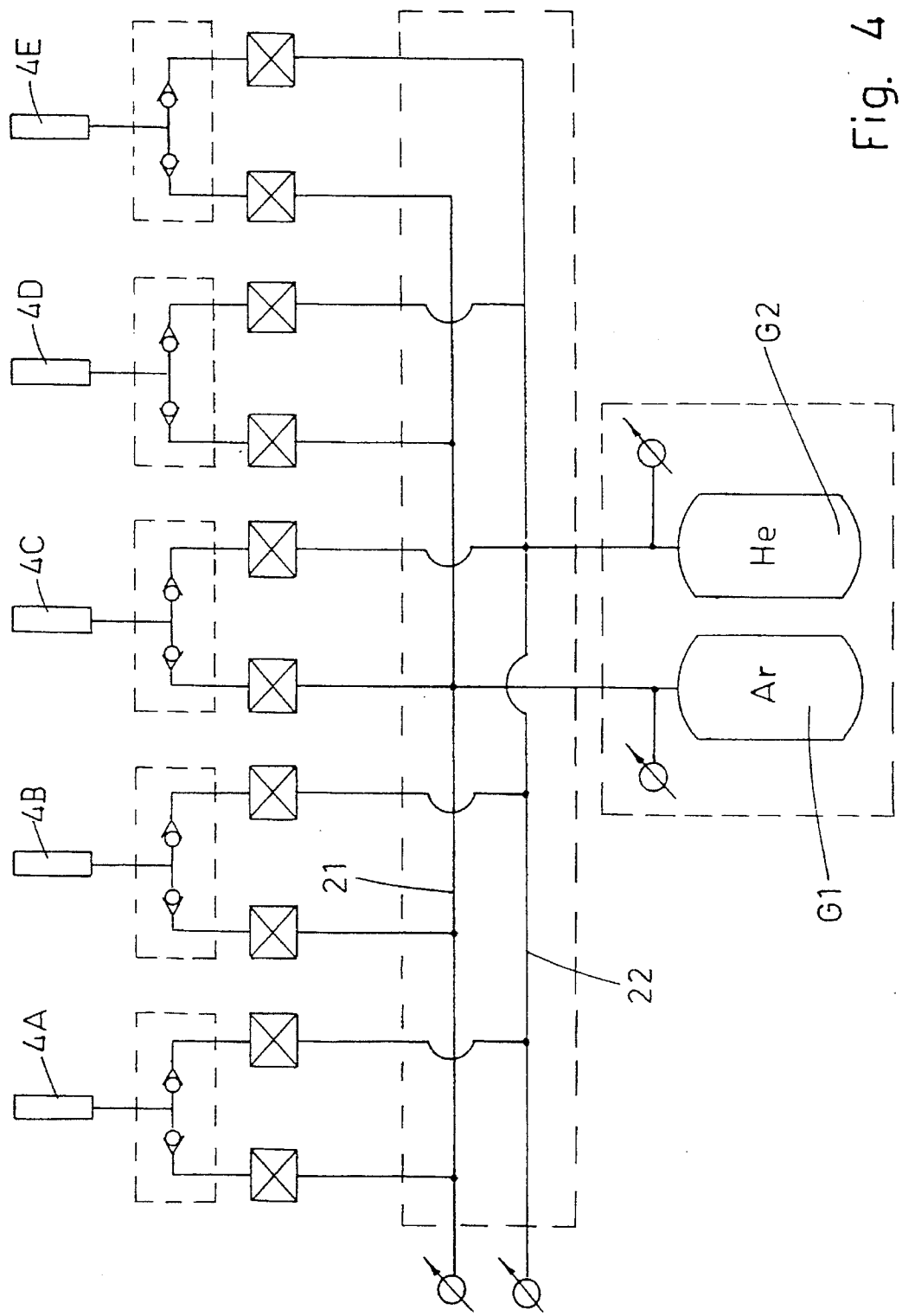
FIG. 4 schematically illustrates the gas flow arrangement of the various probes in the apparatus.

In FIG. 4 the gas flow scheme can be seen. G1 represent the first gas reservoir (e.g., argon), and G2 the second gas reservoir (e.g., helium). G1 is connected to supply line 21, and G2 to supply line 22, which supply the gas to the probes, as needed. All probes, 4A–4E, are connected to the supply lines 21 and 22, and draw gas as needed.

Figure 5:
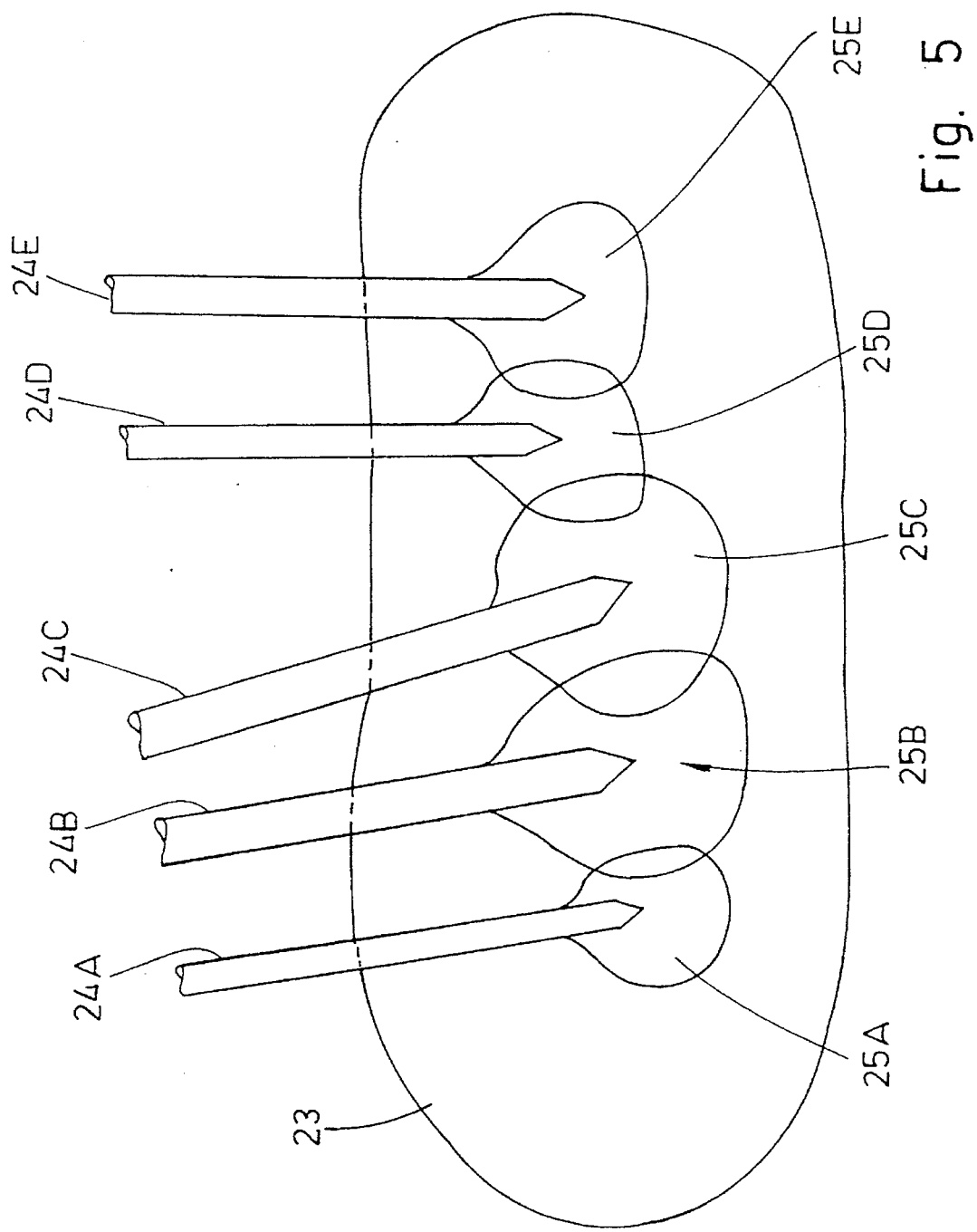
FIG. 5 schematically shows the effect of a plurality of probes in the treatment of an organ.

In FIG. 5 there is schematically shown an intervention on an internal organ, e.g., the liver 23. Each of the five probes 24A–24E shown in the figure, independently generates a ball-like frozen area around its contact area, indicated by 25A–15E, respectively. Therefore, positioning the probes near and around an area to be treated, e.g., a tumor, permits to freeze a desired volume at the same time. While it has been found that using five probes is particularly convenient, the invention is by no means limited to this number, and less or more probes can of course be used.

All the above description and examples have been provided for the purpose of illustration, and are not intended to limit the invention in any way. Many modifications can be effected in the various parts, shape and construction of the apparatus of the invention, different and additional functions can be performed by the apparatus described above, all without exceeding the scope of the invention.

We claim:

1. Cryogenic surgical apparatus comprising:
   a) a plurality of probes, each having a contact surface, each of which probes is suitable for creating fast temperature changes at the contact surface, each of said probes comprising:
   1) heating exchanging means coupled to an orifice, the orifice opening into conduit means;
   2) conduit means in contact with the surface to be heated and cooled, the conduit means being suitable to allow a flow of a fluid in contact with the surface to be heated and cooled;
   3) two independent connections for pressurized gas sources, connected to the heat exchanger;
   b) two independent pressurized gas sources, connected to the probe through the two independent connections;
   c) controllable gas flow valves to permit or preclude a flow of each of the gases from the independent pressurized gas sources into the probe;
   d) control means, to control the controllable gas flow rate valves according to desired probe temperatures;
   e) temperature generation means, coupled to each of the probes, being capable of creating cryogenic and above 0° C. temperatures at the contact surface of the probe; and
   f) temperature control means, to control the temperature generation means.

2. Apparatus according to claim 1, wherein the temperature control means control the temperature of the contact surface of each probe, independently, in the range −170° C. to +70° C.

3. Apparatus according to claim 2, further comprising display means to display temperature and status data for each of the plurality of probes.

4. Apparatus according to claim 3, wherein the status for each probe is independently selectable from: 1) OFF; 2) STICK; 3) FREEZE and 4) THAW.

5. Apparatus according to claim 4, further comprising temperature-reading means located at or near the contact surface of each probe, which temperature-reading means provide temperature readings to the control means.

6. Apparatus according to claim 5, wherein the temperature-reading means comprise one or more thermocouples.

7. Apparatus according to claim 6, further comprising pressure-reading means located between the two independent pressurized gas sources and the probe, to provide to processing means readings corresponding to pressure supplied by each of the two independent pressurized gas source.

8. Apparatus according to claim 7, wherein the pressure-reading means read the working pressure on the gas line(s).

9. Apparatus according to claim 7, wherein the pressure-reading means read the pressure in the gas reservoir(s).

10. Apparatus according to claim 9, wherein each probe is operated by switch(es) provided on the probe itself.

11. Apparatus according to claim 9, comprising one switch for each of the FREEZE, THAW and STICK operations.

12. Apparatus according to claim 11, comprising up to 10 probes.

13. Apparatus according to claim 12, for use in liver surgery.

14. Apparatus according to claim 12, for use in lung surgery.

15. Apparatus according to claim 12, for use in brain surgery.

16. Apparatus according to claim 12, for use in prostate cancer surgery.

* * * * *